(12) United States Patent
Teran et al.

(10) Patent No.: US 7,604,780 B2
(45) Date of Patent: Oct. 20, 2009

(54) OZONE DISINFECTION APPARATUS

(75) Inventors: Alfredo J. Teran, Cape Canaveral, FL (US); Nidal A. Samad, Merritt Island, FL (US); Louis V. Mangiacapra, Mims, FL (US)

(73) Assignee: Agrimond USA Corporation, Rockledge, FL (US)

( * ) Notice: Subject to any disclaimer, the term of this patent is extended or adjusted under 35 U.S.C. 154(b) by 42 days.

(21) Appl. No.: 11/552,694

(22) Filed: Oct. 25, 2006

(65) Prior Publication Data

US 2007/0086913 A1  Apr. 19, 2007

Related U.S. Application Data (63) Continuation-in-part of application No. 11/160,567, filed on Jun. 29, 2005, now abandoned.

(60) Provisional application No. 60/522,830, filed on Nov. 11, 2004, provisional application No. 60/596,861, filed on Oct. 26, 2005.

(51) Int. Cl.
*B05B 7/04* (2006.01)
(52) U.S. Cl. .................. 422/186.07; 422/186.11; 422/186.12; 422/28; 239/398; 239/424.5
(58) Field of Classification Search ............ 422/186.12, 422/28, 186.07, 186.11; 239/398, 424.5
See application file for complete search history.

(56) References Cited

U.S. PATENT DOCUMENTS

| 5,815,869 | A | 10/1998 | Hopkins |
| 9,455,017 | | 9/2002 | Kasting, Jr. et al. |
| 6,591,845 | B1 * | 7/2003 | Bergman et al. ......... 134/100.1 |
| 6,982,006 | B1 | 1/2006 | Boyers et al. |
| 2004/0096354 | A1 * | 5/2004 | Nomura et al. ............... 422/23 |

FOREIGN PATENT DOCUMENTS

JP  410014844 A  *  1/1998

OTHER PUBLICATIONS

English language machine translation of JP410014844A; "Washing and Disinfecting Device for Dish and Other Tableware"; inventor: Nakatani; http://www19.ipdl.inpit.go.jp/PA1/cgi-bin/PA1INIT?1183991593102.*

* cited by examiner

*Primary Examiner*—Sean E Conley
(74) *Attorney, Agent, or Firm*—Ronald E. Smith; Smith & Hopen, P.A.

(57) ABSTRACT

An ozone disinfection apparatus is provided whereby the ozone is dispersed in a vapor. The use of an ozonated vapor increases saturation of the article, surface or area being disinfected. Ozone from a generator on-board the apparatus is forced into contact with a fluid, such as water, to form the vapor. Particle size of the vapor is controlled by passing the vapor through an atomizer.

15 Claims, 7 Drawing Sheets

OZONE DISINFECTION APPARATUS

CROSS REFERENCE TO RELATED APPLICATIONS

This application is a Continuation-in-Part of co-pending U.S. patent application Ser. No. 11/160,567, filed Jun. 29, 2005; which claims priority to U.S. Provisional Patent Application 60/522,830, filed Nov. 11, 2004; and this application claims priority to currently pending U.S. Provisional Patent Application 60/596,861, filed Oct. 26, 2005.

FIELD OF INVENTION

This invention relates to the disinfection of articles and surfaces using ozone.

BACKGROUND OF THE INVENTION

The new reality of this century is that we are living in a world where airborne hazards of pathogenic microorganisms are a major threat to populations. Whether natural occurrences, industry, terrorism, or warfare causes the threat, it represents an ever-present concern. Attention has been directed to the decontamination of buildings, hospitals, post offices, nursing homes, laboratories, subways, trains, airplanes, structures, equipment, facilities, and even personnel. Over many years, various highly dangerous biological warfare agents have been developed. Many nations possess large stockpiles of these agents.

There is a need for effective and quick decontamination technology for biological agents. Although numerous other technologies exist, the primary method is chlorine in the form of a hypochlorite solution that is either sprayed or applied on the object requiring decontamination. Other technologies utilize chemicals, such as chlorine dioxide, hydrogen peroxide, methyl bromide and the like. The current technologies have problems such as corrosion, non-effectiveness in low concentrations or quantities, toxic by-products, collateral damage to equipment and items within a facility or building, and logistical issues.

Each of these chemicals requires extensive training and safeguards for hazardous materials handling and storage including costly permits for purchasing in addition to handling and storage. In higher concentrations required for rapid and complete disinfection they pose a real and dangerous threat if not stored or handled properly. Additional hazards exist during and even after their use as the area must receive additional cleaning to remove the disinfectant before occupancy.

One problem with current decontamination technologies is the size and bulkiness of the current systems causing logistical issues and handling/maneuvering inconveniences. Therefore, what is needed is an efficacious, reliable, and yet compact decontamination system which does not rely on hazardous chemicals which present long exposure risks.

SUMMARY OF INVENTION

In one embodiment, the present invention includes an apparatus for disinfecting articles and surfaces using an ozonated vapor. The apparatus includes an ozone source. An ozone conduit is communicatively coupled to the ozone source and has a discharge at the other end. A liquid reservoir, which most commonly stores water, is communicatively coupled with the ozone conduit so that the fluid in the reservoir enters the ozone conduit as ozone passes through it. An atomizer disposed on the discharge of the ozone conduit converts the fluid from the ozone conduit into a vapor as the fluid and ozone pass through it. An absorption area adjacent the atomizer is adapted to allow absorption of the ozone from the atomizer by the vapor. The ozonated vapor is then dispensed through a vapor ejection port such as a hand-held wand, a spray bar, a nozzle and an aperture formed in the apparatus.

In an alternate embodiment, the fluid reservoir disposed at the end of the ozone conduit opposite the ozone source such that ozone leaving the ozone conduit is forced into contact with the fluid in the reservoir forming the ozonated vapor. A vapor chamber in fluid communication with the fluid reservoir is adapted to receive the ozonated vapor from the fluid reservoir. In this embodiment, the atomizer is disposed between the vapor chamber and the vapor ejection port and is adapted to reduce the size of the ozonated vapor particles passing through it. In an alternate embodiment, the ozone conduit extends to a point above the level of the fluid in the reservoir and an ozone chamber provides the fluid communication from the ozone conduit to the fluid reservoir but prevents fluid communication between the ozone conduit and the vapor chamber.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
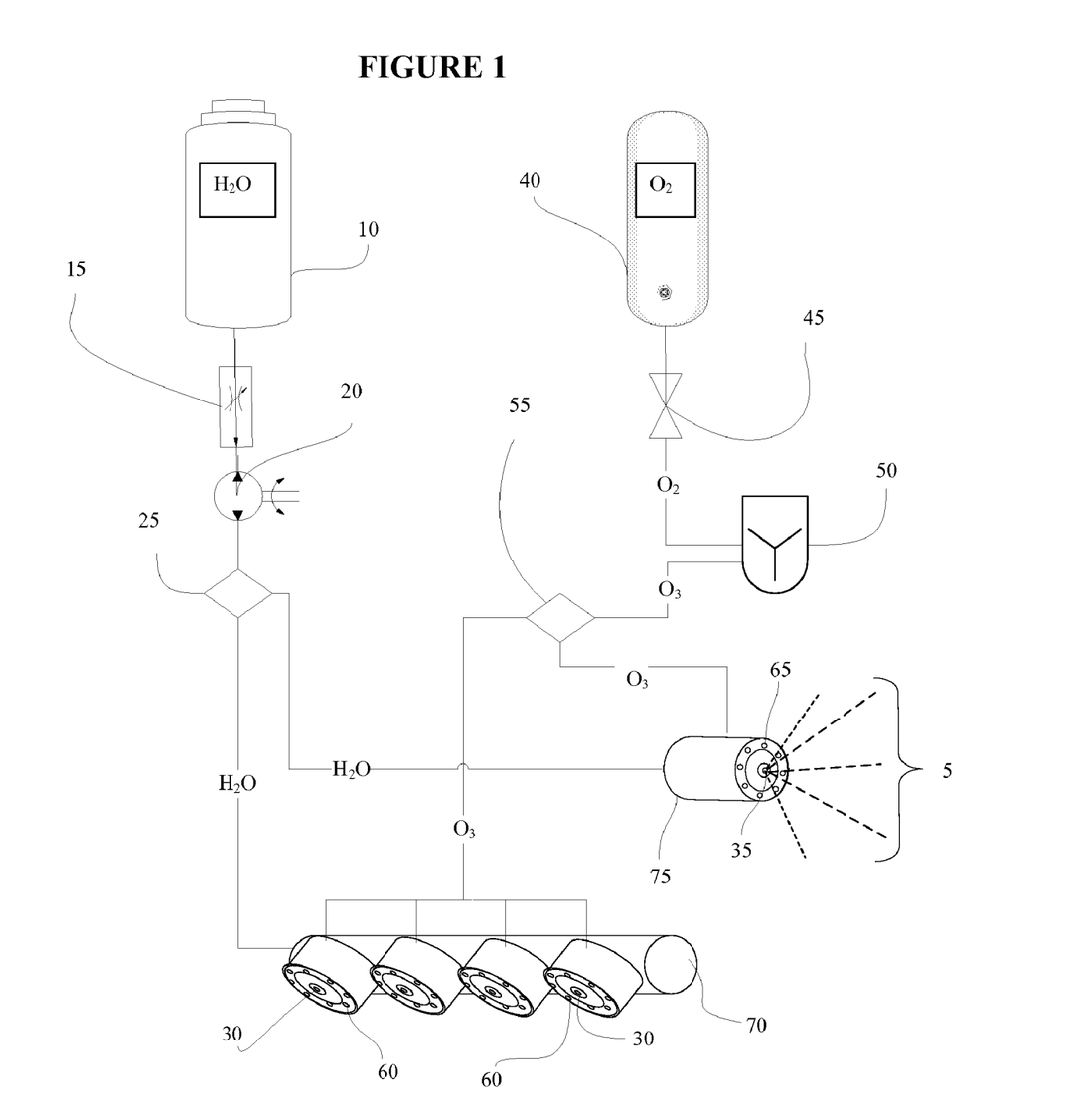
FIG. 1 is a diagram of the inventive apparatus indicating the flow of water through the water subsystem.

Turning now to FIG. 1, a system embodying the present invention includes a water subsystem comprising water source 10, pump 20, water manifold 25, floor water-ejection unit 70 (such as a spray bar) and/or hand held wand 75. Floor dispensing unit 70 is equipped with a plurality of nozzles which have water ejection ports 30, which create mist area 5, surrounded by ozone ejection ports 60. Similarly, hand held wand 75 is equipped with a nozzle which has a water ejection port 35 surrounded by ozone ejection ports 65. The water source can be any water source whereby water enters the system, for example a reservoir or universal hose connector attached to municipal water supply system. In such an embodiment, the water subsystem can be adapted with check valve 15 which prevents backflow.

Furthermore, a filtration subsystem can be incorporated into the water subsystem. A filtration subsystem can include a sediment/particulate filter for mechanical filtration and a carbon filter for chemical filtration. Reverse osmosis or distilled water can also be used as a water source. In this manner, incoming water can be freed of undesirable particulate matter, minerals, and/or chemical agents which would compete with the ozone as an oxidizer, such as chlorine, or otherwise interfere with the action of the ozone. As used herein, a manifold is any device, pipe, or chamber having multiple apertures for making connections as is known in the art.

Pump 20 provides the mechanical force by which water moves through the subsystem. Pump 20 further comprises an inlet port, outlet port, and an electric motor that powers the pump. Pump 20 must provide sufficient force to provide the necessary delivery pressure and flow requirements of the system.

Water leaving the pump through the outlet port can be directed to water manifold 25 which provides a variable connection point among the different plumbing lines and components downstream of pump 20. Flow through water manifold 25 is determined by a flow switch. A pressure gauge can be associated with the manifold to provide a visual indication of the water subsystem's internal pressure. From water manifold 25, water can be selectively directed between floor water-ejection unit 70 and hand-held wand 75. Both water ejection units (70 and 75) can be equipped with a nebulizer such that the water is converted into a fine mist (atomized). As used herein, a nebulizer is any device which converts a liquid to a fine mist. The flow of water from hand held wand dispensing unit 75 (via water ejection port 35) is indicated in FIG. 1 by the numerical indicator 5. Flow through the water subsystem can be controlled via the use of any manifold means, such as solenoid valves, as is well-known in the art.

Figure 2:
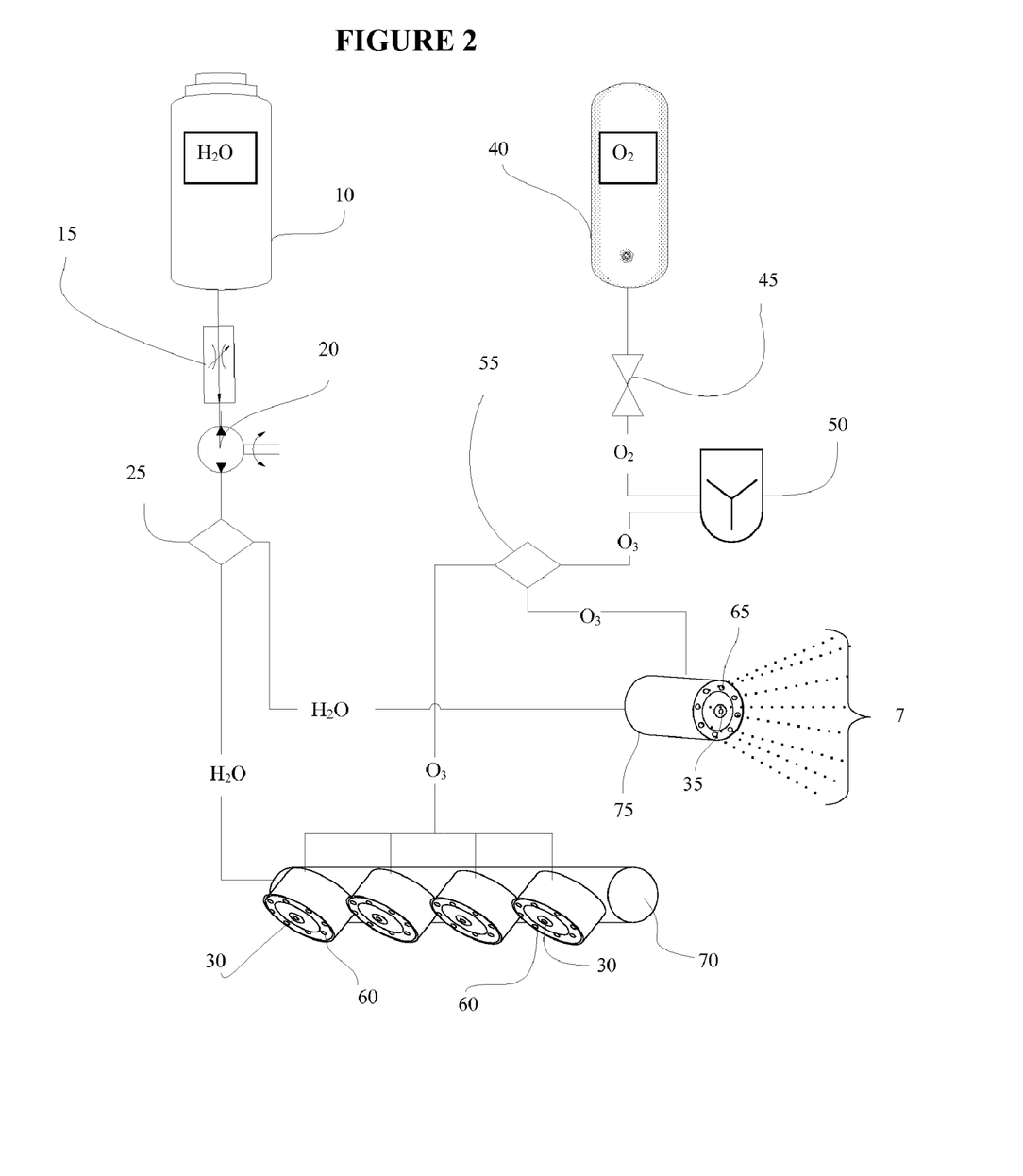
FIG. 2 is a diagram of the inventive apparatus indicating the flow of ozone through the ozone subsystem.

The present invention likewise includes an ozone subsystem comprising oxygen source 40, ozone generator 50, ozone manifold 55, floor ozone injection ports 60 and wand ozone injection ports 65. The ozone for the system is created by the ozone generator which receives oxygen from either a canister containing pure oxygen or from air that has been dried in an air dryer (not shown) since moisture can interfere with the production of ozone. Gas supply valve 45 can be used to direct the flow of oxygen from alternate sources. Any manifold means, such as solenoid valves can be used to direct the flow of ozone through the ozone subsystem.

As with the water subsystem, the ozone subsystem can be equipped with ozone manifold 55, which selectively directs the flow of ozone between the respective ozone injection ports (60 and 65). In one embodiment, water manifold 25 and ozone manifold 55 are communicatively coupled such that the flow of water remains coincident with that of ozone flow. The flow of ozone from the hand held wand dispensing 75 (via ozone injection ports 65) unit is indicated in FIG. 2 by the numerical indicator 7.

Figure 3:
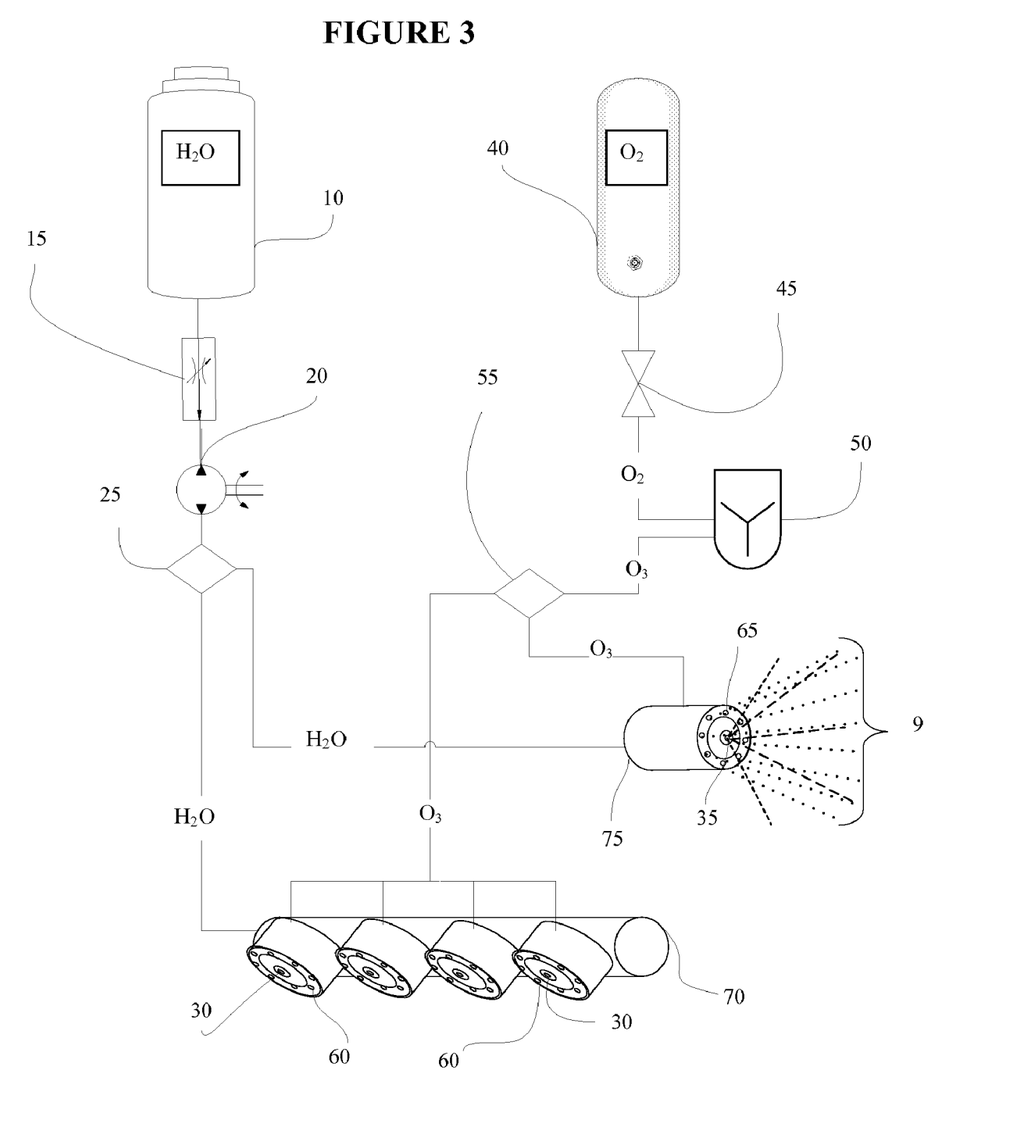
FIG. 3 is a diagram of the inventive apparatus showing the integration of the water and ozone subsystems focusing on the inter-relation of the ozone injection ports and the water ejection ports.
Figure 4:
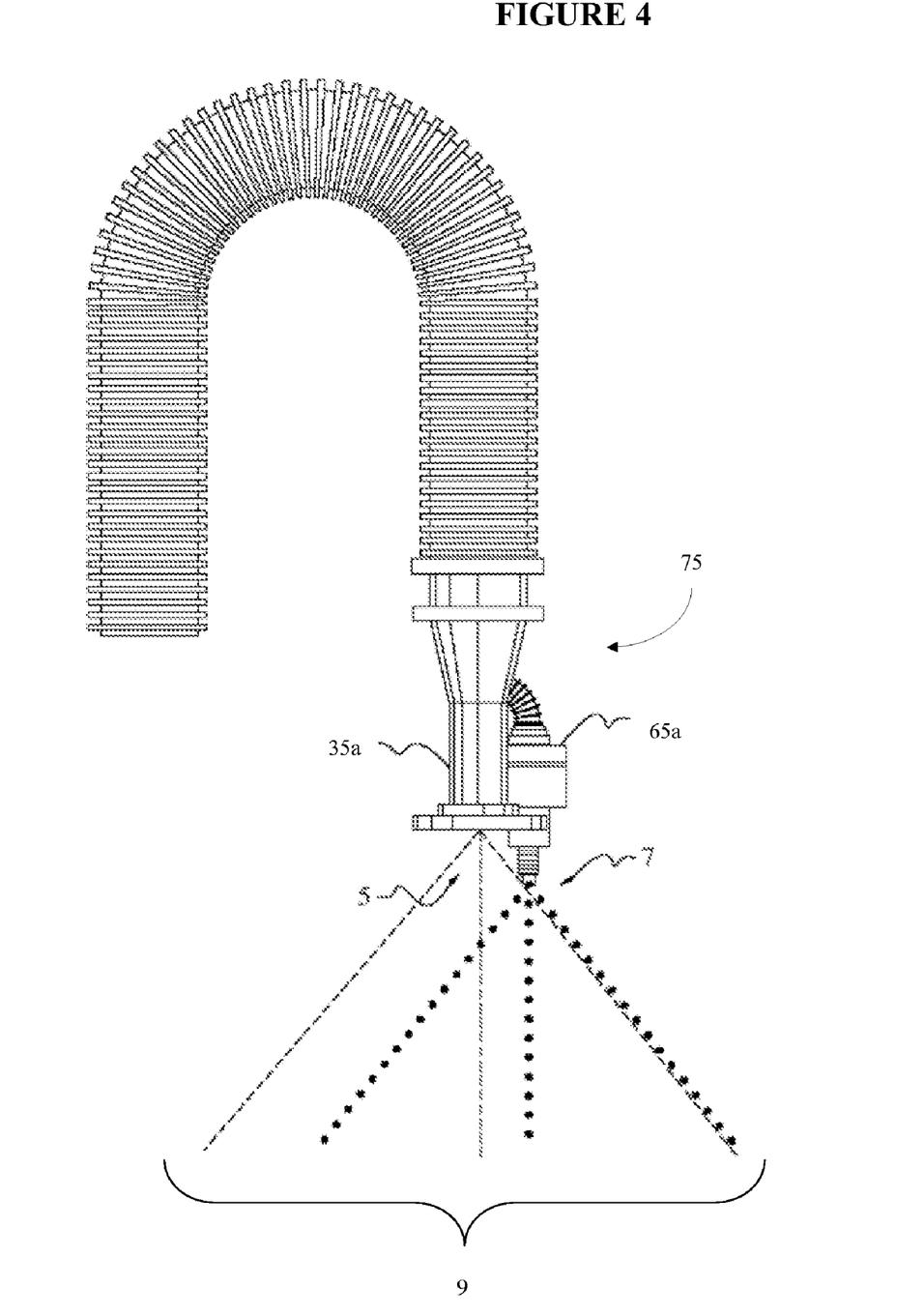
FIG. 4 is a perspective view of one configuration of the hand held wand showing the inter-relation of the ozone injection unit and the water ejection unit.

As it can be seen in FIGS. 2 through 4, ozone 7 is delivered at, or into, the mist area 5 exiting water ejection unit. Mist particle size plays an important role in how much ozone 7 is dissolve in the water mist 5. The higher the dissolved concentration of ozone within the mist, the more effective the disinfection will be. Higher concentrations of ozone also correlate to quicker decontamination times. In one embodiment the preferred mist particle size range is about 15 to 100 microns. Mist particle size outside this range is contemplated by this invention. The concentration of dissolved ozone within the mist is inversely proportional to the particle size. Accordingly, ozone concentration in the mist may only reach 1 mg/liter.

Figure 5:
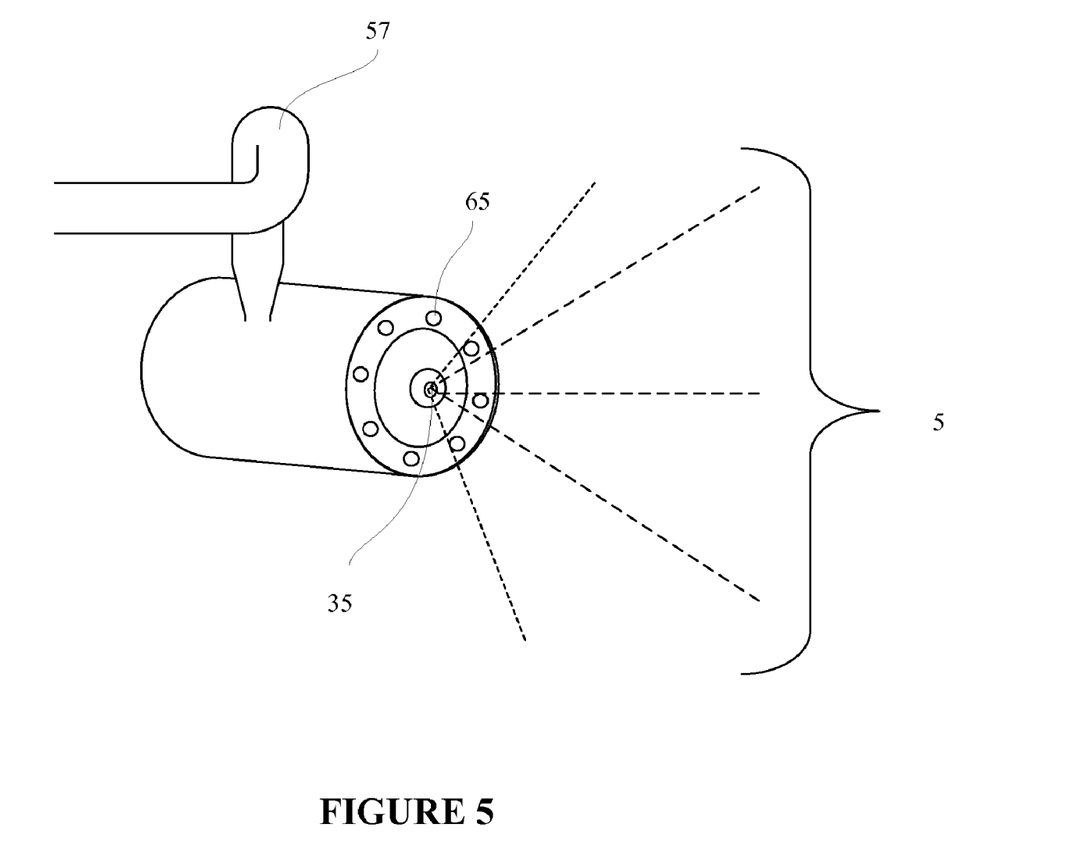
FIG. 5 is a perspective view of an alternate configuration of the hand held wand showing the inter-relation of the ozone injection ports and the water ejection port.

FIGS. 4 and 5 show alternate arrangements of water ejection in relation to ozone injection. Alternate configurations are acceptable, and contemplated. A skilled artisan can envision different, and equivalent, configurations and change the locations of some, or all, of the individual components without deviating from the spirit and teachings of the invention.

In FIG. 4 hand held wand 75 has water nozzle 35a adjacent, and in coincident relation, to ozone injection unit 65a. In contrast, the arrangement in FIG. 5 offers a configuration offering greater saturation of ozone in the water mist. Here, water is dispensed through water ejection port 35. Ozone is fed through conduit 57 to ozone injection ports 65 which are spaced radially about water ejection port 30 ensuring a broad range of contact between the ozone and water 9.

The hand held wand is useful where the system is used for decontamination on elevated surfaces (i.e. walls, countertops, shelves, cabinet doors, etc.). The wand may also be used for decontamination of hard to reach areas without regard to their elevation. The wand is activated by flipping the flow-selection switch; water and ozone are then diverted from the floor subsystem to the wand subsystem.

In one embodiment of the invention, a minimum of about 10 mg/liter of dissolved ozone within the mist is achieved. In this manner, the target bacteria in viable or spore formation are exposed to a moisture rich environment and become exposed to the aqueous and gaseous ozone. Thereby, a double exposure to the powerful oxidant, ozone, is achieved.

The system, as disclosed, uses a very small amount of water and requires less energy than a small hair dryer to operate. One hour of continuous operation requires less than 2 liters of water. Tests using the present invention resulted in a complete (100%) destruction of $10^6$ count of viable *stahylococcus aureus* and *pseudomonas aeruginosa* in 12 seconds of treatment. More than a 90 percent reduction in Anthrax stimulant spore count was achieved during the same time period in subsequent tests.

The invention delivers the disinfecting agent, ozone, in the form of a vapor. The use of an ozonated vapor increases the saturation of the article or surface to be cleaned with ozone. Additionally, the use of an ozonated vapor increases the inventions effectiveness against spore-forming pathogens, such as Anthrax. Some pathogens form protective spores in response to unfavorable conditions, such as starvation and dehydration. The resulting spore is metabolically dormant and is extremely resistant to chemical and physical attacks. The spore retains the ability to revive almost immediately when favorable conditions return to the environment. The use of ozonated vapor, due to its high humidity, degrades the she shell-like spore thereby exposing the pathogen to the ozone; thereby destroying the cell. As used herein, the term "vapor" refers to a substantially gas phase in a state of equilibrium with identical matter in a liquid or solid state below its boiling point.

The ozonated vapor is created by passing a stream of the liquid past a fine fluid-metering component, or atomizer. The host fluid, supplied by the fluid reservoir, can be accelerated (or compressed), such as by passing it through a venturi or under pressure. In one embodiment, the operator controls the amount of fluid, and thereby the density of the vapor, using a variable control which passes more or less of the fluid in the reservoir through the atomizer. As used herein, an "atomizer" is any device adapted to convert a fluid into a vapor.

EXAMPLE 1

Figure 6:
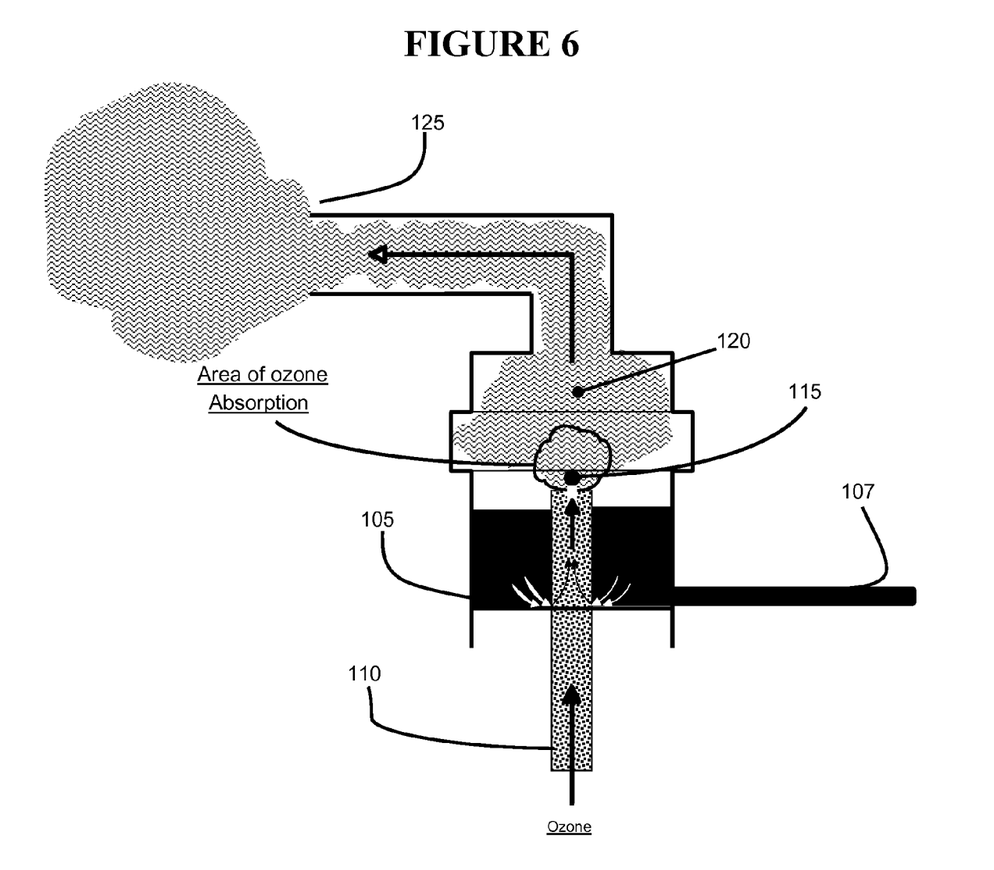
FIG. 6 is a diagram of the nebulizer of one embodiment of the invention.
Figure 7:
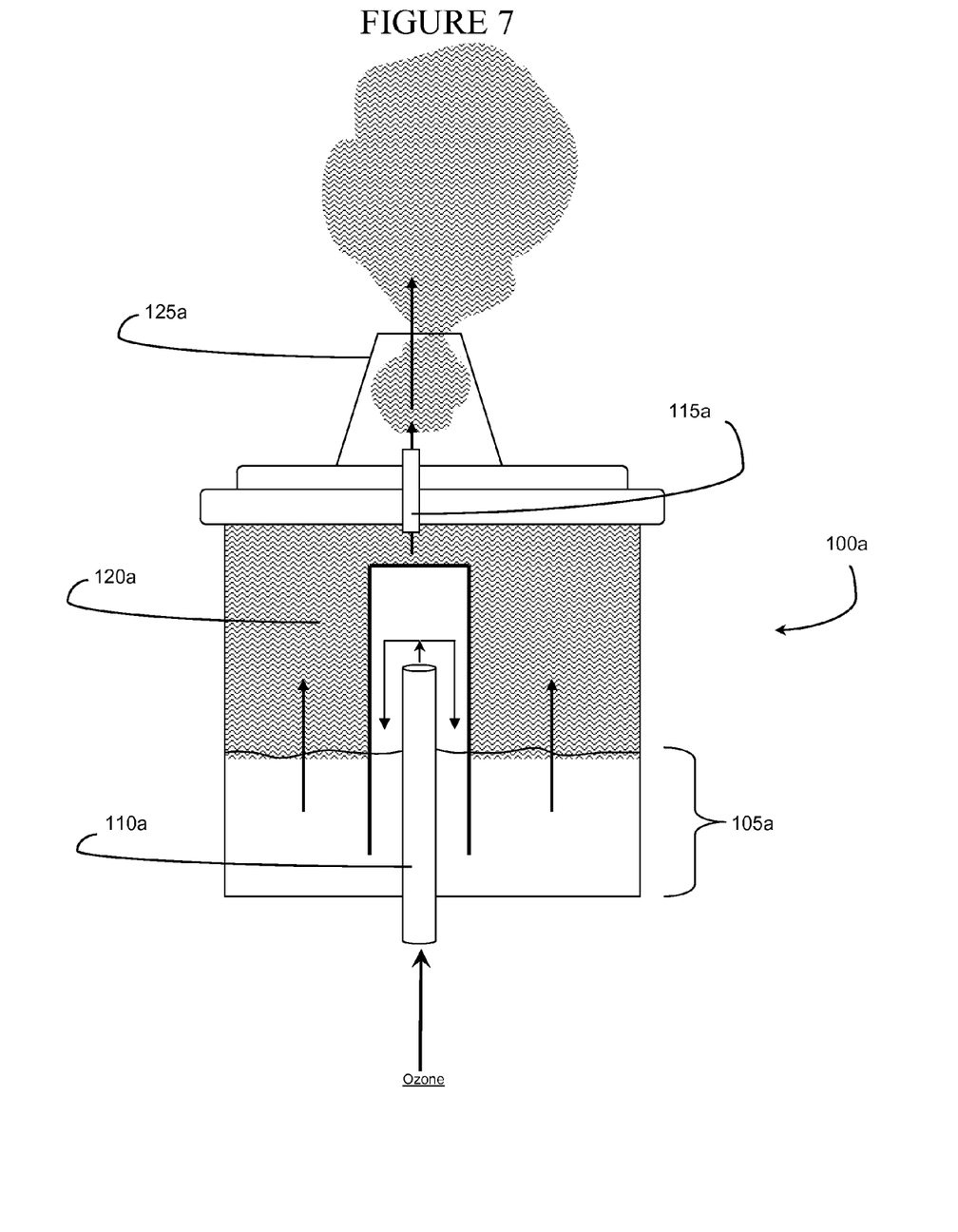
FIG. 7 is a diagram of the nebulizer of an alternate embodiment of the invention.

In one embodiment, nebulizer 100, as demonstrated in FIG. 6, generates ozonated water vapor, or fog 120. Water reservoir 105 is in fluid contact with ozone conduit 110. The end of ozone conduit 110 is equipped with atomizer 115. During operation ozone passes through conduit 110. A small volume of water from reservoir 105 enters conduit 110 as the ozone passes through. The ozone and water combination is vaporized as it engages atomizer 115. The ozone is absorbed by the vaporized water and eventually becomes dissolved therein; thereby forming the ozonated water vapor 120. Water conduit 107 can be added to the system to replace water lost from the reservoir as vapor 120 is created.

Vapor 120 then exits the device at ejection port 125 for delivery. Vapor 120 can be dispersed via any known device such as, but not limited to, the hand-held wand, spray bar, or can even be allowed to exit via an open conduit to permeate any room or space. The use of an ozonated fog has applications independent of the apparatus disclosed herein and can be used as a stand-alone method of disinfection.

EXAMPLE 2

Other embodiments of the above described method are envisioned using any know nebulizer. For example, FIG. 7 shows alternate nebulizer 100*a*. Ozone leaving ozone conduit 110*a* enters the water contained in water reservoir 105*a*. Through diffusion and the pressure from conduit 110*a*, ozonated mist 125*a* forms within the apparatus where it is either dispersed through ejection port 125*a*. Alternatively, atomizer 115*a* can be adapted within the device to reduce the particle size of vapor 120*a*.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A disinfection apparatus comprising:

an ozone source;

an ozone conduit having an intake end communicatively coupled to the ozone source and a discharge end;

a liquid reservoir in fluid communication with the ozone conduit, such that the ozone conduit is at least partially disposed within the liquid reservoir, the liquid from the liquid reservoir enters the ozone conduit as ozone passes therethrough, and the liquid and ozone mix to create an ozonated fluid; and an atomizer to convert the ozonated fluid in the ozone conduit into a vapor as the ozonated fluid passes therethrough.

2. The apparatus of claim 1, further comprising an absorption area positioned adjacent to the atomizer such that the absorption area allows absorption of ozone by the vapor.

3. The apparatus of claim 1, wherein the atomizer is disposed at the discharge end of the ozone conduit.

4. The apparatus of claim 1, further comprising a vapor ejection device selected from the group consisting of a hand-held wand, a spray bar, a nozzle and an aperture formed in the apparatus.

5. The apparatus of claim 1, wherein the liquid reservoir is disposed in fluid communication with the ozone conduit such that the liquid from the liquid reservoir enters the ozone conduit at a location between the intake end and the discharge end as ozone passes therethrough.

6. The apparatus of claim 1, wherein the liquid reservoir is disposed in fluid communication with the ozone conduit such that ozone leaving the ozone conduit is dissolved in the liquid in the liquid reservoir forming an ozonated fluid.

7. The apparatus of claim 6, further comprising:

a vapor chamber in fluid communication with the liquid reservoir adapted to receive the ozonated fluid from the liquid reservoir; and a vapor ejection device.

8. The apparatus of claim 7, wherein the vapor ejection device is selected from the group consisting of a hand-held wand, a spray bar, a nozzle and an aperture formed in the apparatus.

9. The apparatus of claim 8 wherein the atomizer is disposed between the vapor chamber and the vapor ejection device.

10. The apparatus of claim 6, wherein the ozone conduit extends to a point above the level of the liquid in the reservoir.

11. The apparatus of claim 10, further comprising an ozone chamber adapted to provide fluid communication between the ozone conduit and the liquid reservoir and to prevent fluid communication between the ozone conduit and the vapor chamber.

12. A disinfection apparatus comprising:

an ozone source;

an ozone conduit having an intake end communicatively coupled to the ozone source and a discharge end;

a liquid reservoir in fluid communication with the ozone conduit such that the ozone conduit is at least partially disposed within the liquid reservoir, the liquid from the liquid reservoir enters the ozone conduit at a location between the intake end and the discharge end as ozone passes therethrough, and the liquid and ozone mix to create an ozonated fluid;

an atomizer disposed on the discharge end of the ozone conduit;

wherein the atomizer converts the ozonated fluid from the ozone conduit into a vapor as the ozonated fluid passes therethrough; and an absorption area adjacent the atomizer to allow absorption of ozone by the vapor.

13. A disinfection apparatus comprising:

an ozone source adapted to deliver ozone under pressure;

an ozone conduit in fluid communication with the ozone source;

encompass a liquid reservoir disposed such that the ozone conduit is at least partially disposed within the liquid reservoir and the ozone leaving the ozone conduit is dissolved in the liquid in the liquid reservoir forming an ozonated fluid;

a vapor chamber in fluid communication with the fluid reservoir adapted to receive the ozonated fluid from the liquid reservoir; and a vapor ejection device adapted to eject the ozonated liquid from the vapor chamber.

14. The apparatus of claim 13, wherein the ozone conduit extends to a point above the level of the liquid in the liquid reservoir.

15. The apparatus of claim 14, further comprising an ozone chamber adapted to provide fluid communication between the ozone conduit to the liquid reservoir and to prevent fluid communication between the ozone conduit and the vapor chamber.

* * * * *